United States Patent [19]
Sarfarazi

[11] Patent Number: 5,190,057
[45] Date of Patent: Mar. 2, 1993

[54] SARFARAZI METHOD OF CLOSING A CORNEAL INCISION

[76] Inventor: Faezeh Sarfarazi, 25 Wiswall Rd., Newton Center, Mass. 02159

[21] Appl. No.: 807,437

[22] Filed: Dec. 13, 1991

[51] Int. Cl.$^5$ ............................................. A61F 9/00
[52] U.S. Cl. ................................. 128/898; 604/289; 604/294; 606/213; 606/214
[58] Field of Search ................... 606/107, 214, 213; 604/289, 294; 128/76.5, 898

[56] References Cited

U.S. PATENT DOCUMENTS

| | | | |
|---|---|---|---|
| 3,438,374 | 4/1969 | Falb et al. | 606/214 |
| 3,995,641 | 12/1976 | Kronenthal et al. | 606/214 |
| 4,035,334 | 7/1977 | Davydov et al. | 606/231 X |
| 4,414,976 | 11/1983 | Schwarz et al. | 606/214 |
| 4,909,251 | 3/1990 | Seelich | 606/213 |

OTHER PUBLICATIONS

Wood, C. A., *The American Encyclopedia and Dictionary of Ophthalmology*, 1916, pp. 6833-6855.

Tasman, W. & Jaeger, E. A., Duane's Clinical Opthalmology 1990, Ch. 50, pp. 2-3, Ch. 64, pp. 5-6.

Duran, J. A. & Labella, F., Keratoscopy through the Slit Lamp *Ophthalmic Surgery*, 21, No. 11, 1990 pp. 810-811.

Visfvinkel et al., Contact Keratoscope for Clinical and Surgical User, *Int. Ophthal.* 4, 1981, pp. 177-178.

Rowsey et al., Use of Keratoscopy, Slit Lamp Biomicroscopy, and Retinoscopy in the Management of Astigmatism After Penetrating Keratoplasty, *Refractive and Corneal Surgery* 7 1991, pp. 33-41.

*Primary Examiner*—Stephen C. Pellegrino
*Assistant Examiner*—Jeffrey A. Schmidt

[57] ABSTRACT

A method of sealing the corneal incision resulting from cataract surgery is presented. The edges of the incision are maneuvered under a keratoscope until an undistorted corneal surface is obtained. Biological glue is then applied to the maneuvered incision. The seal provides for greatly reduced postoperative astigmatism.

20 Claims, 3 Drawing Sheets

SARFARAZI METHOD OF CLOSING A CORNEAL INCISION

FIELD OF INVENTION

This invention relates to closing ophthalmic incisions to prevent astigmatism and wound leakage.

BACKGROUND OF THE INVENTION

Cataract extraction is the most common ophthalmic surgical procedure performed in the in the United States. During cataract extraction, an incision is made at the edge, of cornea followed by capsulorhexis and removal of the nucleus and lens material by aspiration and irrigation or phacoemulsification techniques. For a decade, replacement of the natural lens with an intraocular lens has allowed for improved postoperative vision. However, subsequent closure of the corneal incision by suturing results in surgically induced astigmatism, compromising the improved vision. The suturing procedure requires surgical skill and is time consuming. The surgically induced astigmatism is between one and eight diopters depending on the surgeon's skill, the size of the incisions and the type of suture used. Presently the amount of time required for suturing is between 15 minutes to 1 hour depending on the skill of the surgeon and technique. Surgically induced astigmatism is not limited to cataract surgery, it also occurs in corneal graft. It has been observed that the tightest sutures produce the greatest amount of astigmatism. The astigmatism requires correction by glasses or contact lenses, otherwise the patient cannot have perfect vision even with the best surgical techniques.

Previous methods of managing the surgically induced astigmatism have included selective suture removal, an adjustable running suture technique, external corrective lenses and addition of compressional sutures.

The amount and placement of an astigmatism can be observed with a keratoscope, an instrument for observing abnormal curvatures of the cornea. The most common form consists of a disc bearing black and white circles, which, in case of anomalous curvature, appear to be distorted figures instead of concentric circles. A more detailed discussion can be found in the American Encyclopedia and Dictionary of Ophthalmology. Of particular interest is a simple hand held keratoscope which can be used with a slit lamp or in the operating room with the microscope, in use since 1974, called a contact keratoscope. It is made of a clear inner cylinder and a white outer cylinder. The white cylinder is engraved with eight lines so that when projected onto a small steel ball, the lines are equal in thickness and equally separated. The contact keratoscope is light in weight and does not noticeably deform the eye when placed on the sclera. It is presently used for surgical correction of high post-keratoplasty astigmatism and thermal wedge resection. A more detailed description and references can be found in Int. Ophthal. 4,3: 177-178, 1981. The keratoscope can be mounted for use with the slit lamp or microscope used during operation. The image projected by the keratoscope can be analyzed by computer. (Such a computer analysis is shown in Duane's Clinical Ophthalmology, 1990, vol 1., Chp. 64, pg. 7.) It is possible that other methods of measuring the surface topography of the eye could be used with the present invention.

Biological glue is a glue derived from fibrinogen, a protein found in the blood which is converted into fibrin during clotting. Fibrin is a white, insoluble fibrous protein which when mixed with thrombin acts as a glue. The fibrin and thrombin are available commercially or the fibrin may be extracted from the patients blood by means of plasmaphoresis (electrophoretic separation of blood components). This glue has been used in nonsuturable hemorrhage, pancreatic injuries, craniofacial surgery, pluro-pulmonary fistula, nerve repairs, control of pulmonary air leaks, obstetrics and gynecology, heart ventricular ruptures, repair of giant scleral ruptures, dental surgery, plastic surgery, epikeratophakia, perforated corneal ulcers, frontobasal and orbital reconstruction following trauma without complications.

After cataract surgery, leakage from the sutured incision can occur. To prevent this a contact lens made from collagen is placed on the eye. Such collagen shields are absorbed by the body after one to three days.

Much of the time required for ophthalmic surgery is occupied with suturing. The time for this procedure can be reduced to 5 min. by the technique of the disclosed invention. Other surgical incisions resulting from ophthalmic surgery are conjuntiva-limbus incision during glaucoma surgery, and scleral-tennon-capsule incision during vitreous retinal surgery.

It is an object of this invention to provide a method of closing the corneal incision which will minimize postoperative astigmatism, minimize required surgical time and skill, and minimized postoperative complications and recovery times.

BRIEF SUMMARY OF THE INVENTION

The present invention provides a method of sealing of the corneal incision after surgery with biological glue under the guidance of a keratoscope.

DESCRIPTION OF THE PREFERRED EMBODIMENTS

The cornea is opened for cataract surgery by an incision 1.5 to 2.0 mm away from the limbus. The size of the incision varies according to surgeon preference, the type of intraocular lens to be implanted and the surgical techniques used for removing the natural lens from the eye.

After removal of the natural lens and its replacement with an intraocular lens, a keratoscope image of the cornea will be provided. The preferred keratoscopes for the operating environment are the hand keratoscope which is built into the surgical microscope.

The surgeon holds the two edges of the corneal incision with two forceps moving them up and down, right or left, until an undistorted pattern is viewed through the microscope-keratoscope. With the edges stabilized in this position, biological glue is applied to the corneal incision, possibly by an assistant, and the edges held for one minute, until the glue has set. The surgeon can make fine adjustments if necessary.

If the incision is large, that is, more than 7 mm. one or more clips or staples such as shown in FIGS. 2 through 8 can be used to hold a portion of the incision closed while a separate section is sealed. Such clips would be small, perhaps 1-2 mm in width, and relatively soft so as to not distort the cornea during use or removal. Although the clip could be made of a soft metal such as gold or a flexible polymer such as an acrylic, it is thought that if a clip or staple could be made of collagen that removal would be unnecessary. The clip could also be made of at least 2 materials, for example, a soft acrylic for the tissue gripping area and a metal for the area where pressure is applied. Perhaps a clip having a removable collagen edge or an edge soluble in the glue could be used. Alternatively, but not preferred, a temporary suture could be used.

Figure 3:
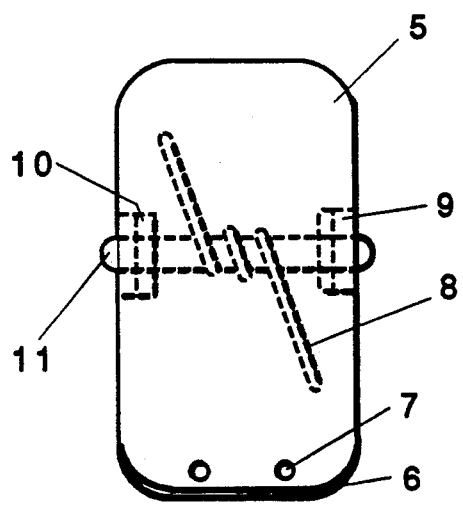
FIG. 3 is a top view of a first embodiment of a clip for use with the present invention.
Figure 4:
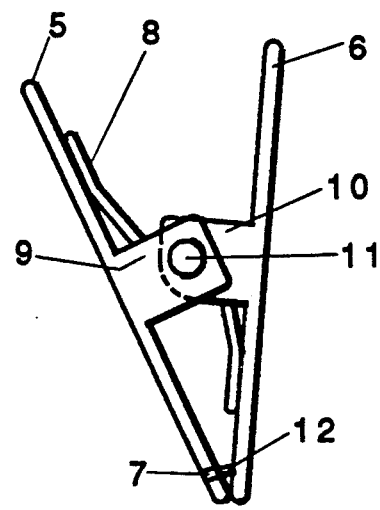
FIG. 4 is a side view of the embodiment of FIG. 3.

FIG. 3 shows a clip having an upper plate 5, a lower plate 6, an upper pivot shaft support 9, a lower pivot shaft support 10, a pivot shaft 11, and a spring 8. The gripping end of the pin is equipped with two protrusions 12 to grip the tissue, and an recess or Opening 7 for accepting the protrusions.

Figure 8:
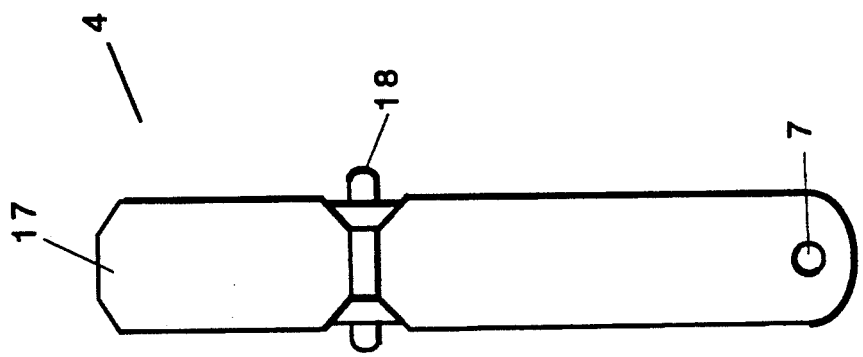
FIG. 8 is a top view of the second embodiment.
Figure 7:
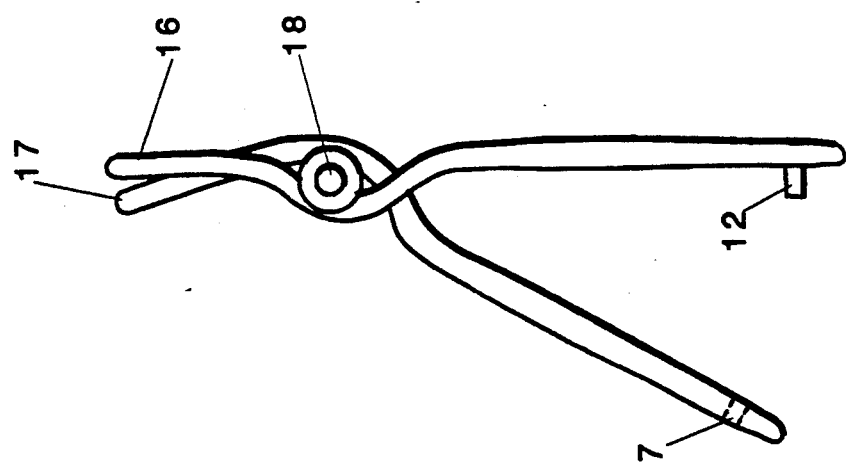
FIG. 7 is a side view of the second embodiment in an opened position.
Figure 6:
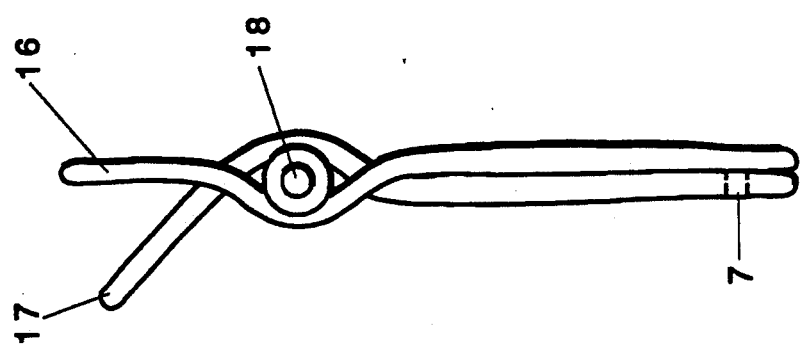
FIG. 6 is a side view a second embodiment of a clip for use with the present invention in a closed position.

FIGS. 6 to 8 show an alternative clip 4 having an angled upper plate 17 and a lower plate 16, interwoven around a pivot shaft 18.

Figure 5:
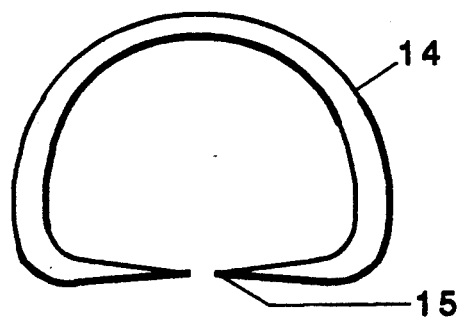
FIG. 5 is a view of a staple for use with the present invention.

FIG. 5 shows a small surgical staple having an arched upper portion 14 and a pointed linear lower portion 15. If made of a resilient material, the ring could be opened over the edges of the tissue, catching one edge at a time, and then allow to resume a unopened position, bringing the edges together. This design would allow the edges to be brought together without being pinched.

Figure 1:
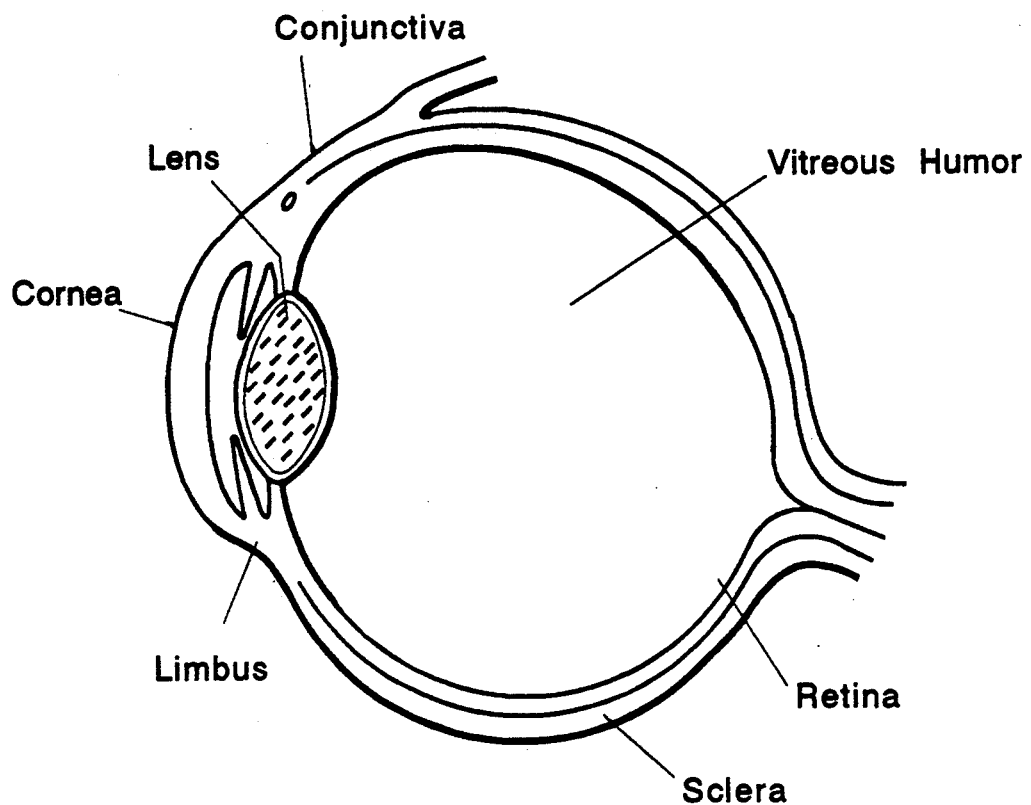
FIG. 1 is a cross-sectional view of the eye.
Figure 2:
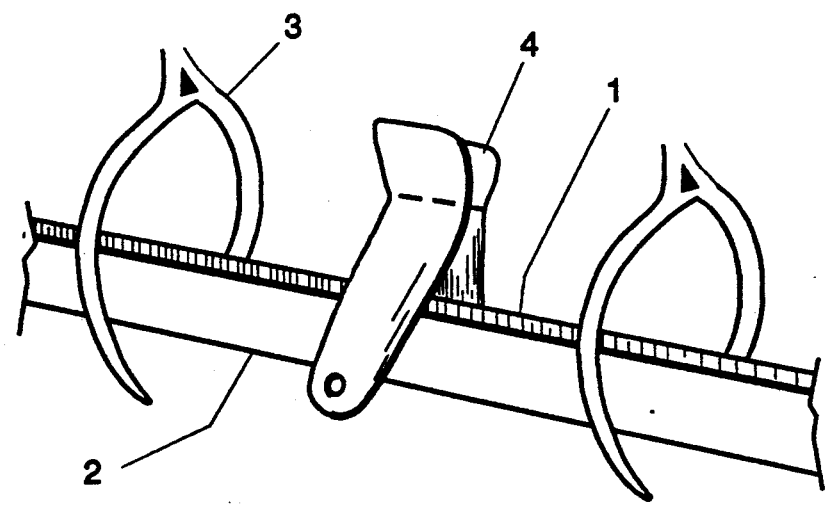
FIG. 2 is perspective view of a the clip shown in FIGS. 6–8, in use.

FIG. 2 shows the clip 4 in use during surgery. The surgeon has grasped the sections of tissue, 1 and 2, with the forceps An assistant then places the clip 4 between the forceps and the surgeon can make further alignment adjustments around the clip.

To make the glue, fibrinogen, preferably extracted from the patients blood, is dissolved in saline solution. Commercially available topical thrombin is then added to form the glue.

Fibrin based glue is believed to have some antibacterial action naturally, however, antibiotics may be added to the glue for enhanced antibacterial action. Such direct contact increases the effectiveness of the antibiotics and lowers systemic reactions relative to antibiotics which are given orally or intravenously.

The glue could also be used to seal incisions between the conjunctiva and limbus after glaucoma surgery, and for the sclera, tenon, or conjuntiva after vitreous retina surgery or other ophthalmic procedures. Because the sclera is somewhat rigid, it is foreseen that the use of the clips, a temporary suture or a staple might be advantageous.

Surgically, incisions closed by the disclosed method would be less costly. Since operating time is reduced, surgeon, anesthesiologist and related fees are reduced. Requirement for corrective lenses would be reduced. Recovery time should be reduced drastically, reducing the number or required postoperative visits and work absence for the patient.

Medically the operation would become safer. The glue is safe, and has anastomosis (the union of tissue to form a network) effects on the vessels of the conjunctiva and episclera, preventing bleeding of vessels after surgery. Postoperative wound leakage after cataract surgery would be prevented due to speedy, tight adhesion of the corneal incision. Patching or eye shields might be unnecessary for patient's eye after surgery. Postoperative vision would be improved. Recovery time would be reduced. The need for collagen shields after surgery could be eliminated, and the amount and duration of postoperative antibiotics would be reduced.

What is claimed is:

1. A method of sealing a corneal incision having edges, which comprises the steps of:
   measuring the curvature of the corneal surface;
   grasping said edges of said incision;
   aligning said edges while remeasuring, such that an undistorted surface is measured;
   applying a glue to said aligned incision; and
   immobilizing said aligned incision for a period of time sufficient to set said glue.

2. The method of claim 1 wherein said glue is a fibrin based glue.

3. The method of claim 2 wherein fibrin for said glue is obtained from a patient'blood.

4. The method of claim 1 wherein said glue contains added antibiotics.

5. The method of claim 1 further comprising the steps of first incising a cornea and extracting a cataract.

6. The method of claim 1 wherein said grasping is done with at least one pair of forceps.

7. The method of claim 1 further comprising the initial step of:
   securing a section of the incision temporarily.

8. The method of claim 7 wherein said section is secured by a fastener chosen from the group consisting of clips, sutures and staples.

9. A method of sealing a corneal incision having edges, which comprises the steps of:
   viewing the corneal surface with a keratoscope;
   grasping said edges of said incision to be joined;
   aligned said edges such that an undistorted image is obtained with said keratoscope;
   applying a glue to said aligned incision; and
   immobilizing said aligned incision for a period of time sufficient to set said glue.

10. The method of claim 9 wherein said keratoscope is a hand held keratoscope.

11. The method of claim 9 wherein said keratoscope is mounted for use in conjunction with an instrument chosen from the group consisting of microscopes and slit lamps.

12. The method of claim 9 wherein said glue is a fibrin based glue.

13. The method of claim 12 wherein said fibrin is obtained from a patient'blood.

14. The method of claim 9 wherein said glue contains added antibiotics.

15. The method of claim 9 further comprising the steps of first incising a cornea and extracting a cataract.

16. The method of claim 9 wherein said grasping is done with at least one pair of forceps.

17. A method of sealing an ophthalmic surgical incision having edges which comprises the steps of:
   grasping said edges of said incision;
   aligning said edges in position for healing;
   placing a glue to said aligned incision; and
   immobilizing said aligned incision for a period of time sufficient to set said glue.

18. The method of claim 17 wherein said incision is an incision in tissues chosen from the group consisting of conjunctival, scleral, limbus, tenon and corneal tissue.

19. The method of claim 17 further comprising the initial step of:

securing a section of the incision temporarily.

20. The method of claim 19 wherein said section is secured by a fastener chosen from the group consisting of clips, sutures and staples.

* * * * *